United States Patent [19]

Coulter et al.

[11] Patent Number: 5,244,913
[45] Date of Patent: Sep. 14, 1993

[54] COMPOSITIONS AND METHODS FOR DISSOLVING BODY CALCULI

[75] Inventors: Stephen L. Coulter; Kenneth G. Mayhan, both of Irvine; Christy L. H. Oviatt, Mission Viejo; Steven R. Morehead, Riverside, all of Calif.

[73] Assignee: Baxter International Inc., Deerfield, Ill.

[21] Appl. No.: 794,544

[22] Filed: Nov. 19, 1991

[51] Int. Cl.⁵ .................... A61K 31/44; A61K 31/14
[52] U.S. Cl. .................................. 514/358; 514/642; 514/643
[58] Field of Search ................ 514/358, 642, 643

[56] References Cited

U.S. PATENT DOCUMENTS

| | | | |
|---|---|---|---|
| 4,096,278 | 6/1978 | Queuille | 424/329 |
| 4,185,088 | 1/1980 | Wagner | 424/78 |
| 4,423,063 | 12/1983 | Rooney et al. | 514/891 |
| 4,759,923 | 7/1988 | Buntin et al. | 424/440 |

OTHER PUBLICATIONS

Chemical Abstract "The Dissolution of Gallstones with Bromoform", Maresova et al, 96, 179–182, 1957.

Mammalian Pathological Chemistry Abstract "Disintegration of Gallstones and Urinary Calculi in Man", Miyake et al., Arch. Surg. 85, 442–455, 1962.

Biological Chemistry Abstract—"Solubilization of Cholesterol Suspensions and Action of Sodium Phenylethylacetate", Amici et al Set. Med 47, 48–52, 1959.

"Dissolution Rates of Cholesterol Monohydrate Crystals and Human Cholesterol Gallstones in Bile Acid-Lecithin Solutions: Enhancing Effect of Added Alkyl Quaternary Ammonium Salts", Higuchi et al, Journal of Pharmaceutical Sci 62(7), 1207–1208, 1973.

"Pigment Gallstone Dissolution by Complex Aqueous Solutions: Effectiveness of Several Co-solvents Studied in Vitro", Wosiewitz, et al, abstract from International Meeting, New Strategies for the Treatment of Biliary Tract Disease, 1988.

"New Solubilizing Mixture for Pigment Gallstones", Patty et al, Gastroenterology, vol. 93, No. 3, Sep. 1987: 665–666.

"Dissolution of Calcium Bilirubinate and Calcium Carbonate Debris Remaining After Methyl tert-Butyl Ether Dissolution of Cholesterol Gallstones", Nelson, et al, Gasteroenterology, 98, 1245–1250.

"Cholesterol Gallstone Dissolution Rate Accelerators I: Exploratory Investigations", Journal of Pharmaceutical Sciences, 66, Aug. 8, 1977, K. H. Kwan et al.

Influence of Benzalkonium Chloride on the Dissolution Rate Behavior of Several Solid-Phase Preparations of Cholesterol in Bile Acid Solutions, Journal of Pharmaceutical Sciences, K. M. Feld et al, 71, 2, Feb. 1982.

"Solvents for Stone Dissolution: Pigment Stones", Leuschner, U. Digestion 39, 100–110, 1988.

"Contact Dissolution of 'mixed' Gallstones: in vitro, MTBE Alternated with N-acetyl Cysteine is More Effective Than When Alternated with Bile Acid--EDTA", Dowling, Clinical Science, 79, Suppl. 1990.

"Dissolution of Human Brown Pigment Biliary Stones", Dai et al, Journal of Hepatology, 9, 301–311, 1989.

"Dissolving Agents of Human Mixed Cholesterol Stones", Dai et al, Gastroenterol Clin Biol, 12, 312–319, 1988.

World Patent Index No. 90/348250/48, Hofmann et al. "Addition of N-acetylcysteine to Aqueous Model Bile Systems Accelerates Dissolution of Cholesterol Gallstones", Niu et al, Gastroenterology, 98, 2, 454–463, 1990, Abstract.

World Patent Index No. 89/166404/23, inventor Leuschner.

World Patent Index No. 83/748638/35, inventor C. Laruelle et al.

W. Swobodnik, "Local litholysis: Dissolution of calcified stones", p. 1, 1990.

Primary Examiner—Marianne M. Cintins
Assistant Examiner—Rebecca Cook
Attorney, Agent, or Firm—Janis C. Henry

[57] ABSTRACT

Compositions and methods for dissolving calculi deposits in humans are disclosed. The compositions include solutions of quaternary ammonium salts and are particularly effective for the contact dissolution of pigment portions of biliary tract calculi such as gallstones. The solutions preferably further include mineral chelating agent and disulfide bond cleaving agent to aid in deaggregating mineral components and glycoprotein components of calculi.

15 Claims, 1 Drawing Sheet

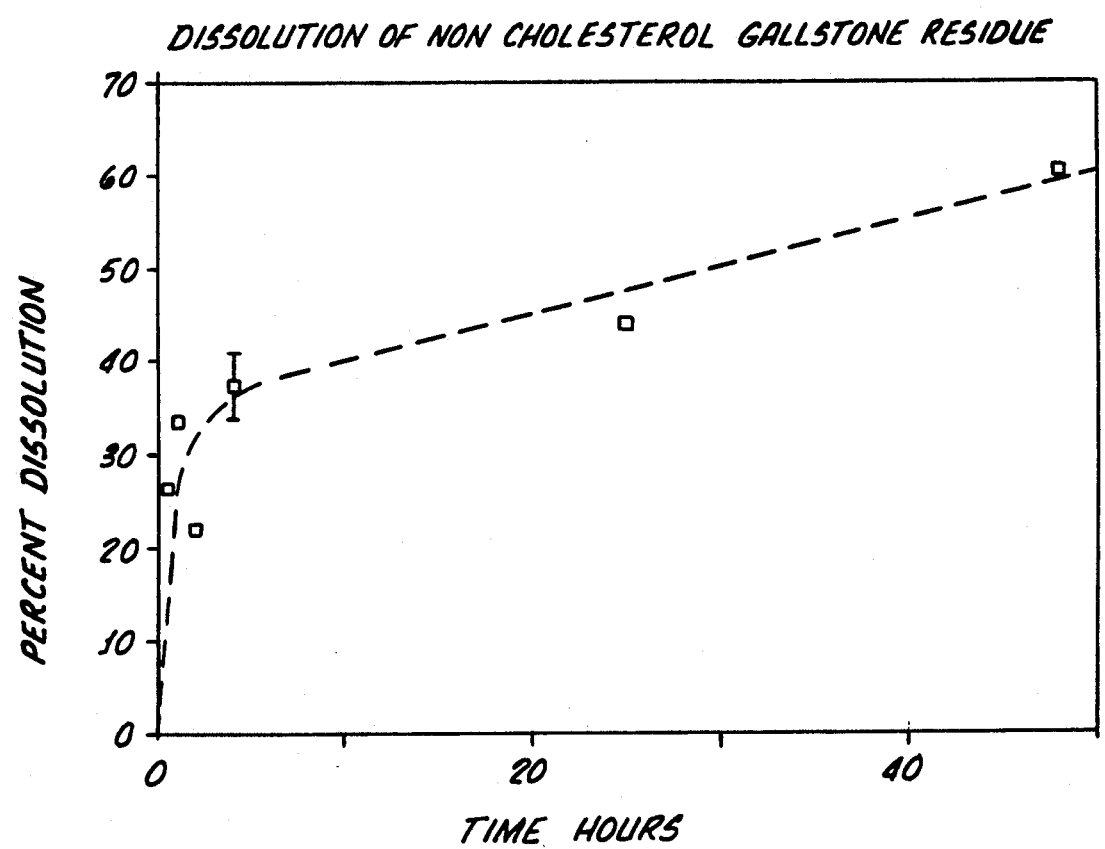

COMPOSITIONS AND METHODS FOR DISSOLVING BODY CALCULI

FIELD OF THE INVENTION

The present invention relates in general to the treatment of diseases characterized by calculi deposits in humans. More particularly, the present invention is directed toward quaternary ammonium salt compositions and methods for using quaternary ammonium salt compositions for the contact dissolution or deaggregation of human gallstones having high pigment content.

BACKGROUND OF THE INVENTION

Each year gallstone disease inflicts large numbers of individuals worldwide. The disease is characterized by biliary colic and is frequently accompanied by obstructive jaundice or pancreatitis. Additionally, patients may experience nausea and vomiting as well as extreme abdominal pain and tenderness. These symptoms are attributed to the presence of calculi, known as biliary tract stones, or gallstones, in the gallbladder or other parts of the biliary tract. A traditional method for treating gallstone disease is to surgically remove the gallbladder with the problematic gallstones remaining intact inside the extracted gallbladder. This procedure, known as cholecystectomy, involves major abdominal surgery and many gallstone disease patients can neither tolerate the surgical intervention nor the traumatic recovery associated with the surgery. Additionally, the high cost of cholecystectomies and long post surgery recovery times make this procedure particularly unattractive.

In recent years many medical practitioners have turned to treatment procedures known as cholelitholysis, or methods for chemically dissolving gallstones. These dissolution techniques initially targeted gallstones having high cholesterol contents. Typically, gallstones suitable for cholelitholysis are at least 75% and generally over 80% cholesterol. One such cholesterol gallstone dissolution method involves orally administering bile acids to patients known to have mostly cholesterol gallstones. This procedure has enjoyed only limited success, and a majority of the patients do not experience complete gallstone dissolution. Moreover, signs of effective gallstone dissolution generally are not apparent until after many months of treatment. Additionally, this method is not practical for patients suffering extreme pain requiring relatively fast relief.

Other cholelitholysis procedures include cholesterol contact dissolution techniques in which solvent capable of dissolving cholesterol is brought into direct contact with gallstones having high cholesterol contents. Typically, this procedure is performed using a percutaneous puncture of the gallbladder with specialized catheters. The gallbladder is then continually irrigated with the solvent which is pumped through the catheter and into the gallbladder. During the irrigation process the cholesterol portion of gallstones gradually dissolves and is withdrawn from the gallbladder in the waste solvent. These treatment methods have the advantage of requiring hours instead of months for dissolution and the patient recovery time is considerably shorter than recovery times associated with cholecystectomy.

The most commonly used procedure involves irrigating the gallbladder with solvents having relatively high cholesterol solubility, such as methyl tert-butyl ether (MTBE). Other solvents and solvent combinations which are reported to have been successfully utilized to dissolve cholesterol gallstones include mixtures of fatty acid and/or alcohol esters of fatty acids (U.S. Pat. No. 4,205,086), mixtures of monooctanoin and diethyl ether (U.S. Pat. No. 4,910,223), and mixtures of fatty acid glycerides and a monoterpene such as d-limonene (U.S. Pat. No. 4,767,783).

In addition to the just described cholelitholysis solvent systems, some researchers have reported that quaternary ammonium salts enhance the dissolution rate of cholesterol when used in conjunction with sodium cholate and lecithin in in vitro experiments (Cholesterol Gallstones Dissolution Rate Accelerators I: Exploratory Investigations, *Journal of Pharmaceutical Sciences*, 66, 8, August 1977, Kwan et al. and Influence of Benzalkonium Chloride on the Dissolution Rate Behavior of Several Solid-Phase Preparations of Cholesterol in Bile Acid Solutions, *Journal of Pharmaceutical Sciences*, 71, 2, February 1982, Feld et al.)

A major problem associated with all these cholelitholysis systems is their ineffectiveness in dissolving noncholesterol gallstones and the noncholesterol components of cholesterol rich gallstones. Cholesterol gallstones almost always contain materials which are not soluble in solvents typically used to dissolve cholesterol. These noncholesterol components not only appear in cholesterol rich gallstones, but can be the major constituent of gallstones. In cholesterol rich gallstones, the noncholesterol components are primarily in the form of calcium bilirubinate, polymerized bilirubin and calcium carbonate. Of these components, the bilirubinates and polymerized bilirubin are frequently collectively referred to as pigment.

Biliary stones which are primarily pigment generally contain small amounts of cholesterol and the calcium bilirubinate and polymerized bilirubin are generally present within a glycoprotein matrix. These gallstones may also contain additional noncholesterol components including calcium carbonate, calcium phosphate, calcium oxalate and calcium fatty acid salts such as calcium palmitate. Depending upon their appearance, density, hardness, and chemical composition, pigment gallstones can be further classified into brown pigmented and black pigmented stones.

Black pigmented stones are generally less than 3 mm in diameter and have a dark rough surface. They are also comparatively hard with a nodular appearance. Brown pigmented stones are significantly softer than the black pigmented stones or the cholesterol rich stones, are lower in density and have a light brown or tan appearance. Their size tends to vary from about 1 mm to about 10–20 mm and often the brown pigmented stones have different geometrical shapes.

Attempts to dissolve noncholesterol components of cholesterol rich gallstones, as well as attempts to dissolve pigmented stones have met with only limited success. Some researchers have tried to dissolve all components of cholesterol rich gallstones by first directly infusing MTBE into the gallbladder or biliary tree to dissolve the cholesterol portion and then infusing aqueous alkaline solutions of ethylenediaminetetraacetic acid (EDTA) and dimethylsulfoxide (DMSO) in an attempt to dissolve the calcium salts and pigment residue portion. (Dissolving Agents of Human Mixed Cholesterol Stones, K. Y. Dai et al., *Gastroenterol Clin Biol*, 1988, 12, 312-319). While showing some reduction in the stone residue, these solutions do not effect significant dissolution.

Other researchers have studied the effects of using combinations of bile acids and EDTA alternating with combinations of MTBE and N-acetyl cysteine (Clinical Science, Dowling, 1990, 79 suppl.). Expanding upon the limited ability of EDTA to dissolve calcium and other mineral complexes left after dissolving the cholesterol in mixed gallstones, others have investigated ionic and nonionic surfactants in combination with EDTA. It is generally recognized, however, that while systems incorporating EDTA contribute to the dissolution of calcium complex components of gallstones, they do not always dissolve sufficient quantities of the pigment and other noncholesterol components of gallstones. Accordingly, EDTA solutions are not consistently clinically reliable for the treatment of gallstone disease.

With respect to dissolving pigment gallstones and other forms of calculi which have largely pigment components and lesser amounts of mineral complexes, solutions variously containing EDTA polysorbates, bile salts, N-acetyl cysteine, monoolein, EDTA or DMSO have been investigated. Varying degrees of success in dissolving these forms of calculi have been reported. The amount to which the dissolution is effected by EDTA depends upon the relative amounts of calcium components, and additional chemical considerations involving the composition of the pigment stones. For example, gallstones frequently exhibit alternating layers of cholesterol, and noncholesterol components. EDTA solutions are generally ineffective in dissolving stones having an outer exposed cholesterol layer, even if the stones have a large calcium complex component.

Accordingly, there is a need to provide compositions and methods for dissolving and/or deaggregating various combinations of calcium carbonate, calcium palmitate, calcium bilirubinate, polybilirubinates, and glycoprotein.

There is also a need to provide compositions for dissolving and/or deaggregating on contact the noncholesterol portions of mixed calculi including the noncholesterol portions of cholesterol gallstones.

There is also a need to provide compositions for dissolving and/or deaggregating on contact pigment calculi including both brown and black pigmented gallstones.

SUMMARY OF THE INVENTION

The present invention accomplishes the above described objectives by providing compositions and methods for effectively dissolving and/or sufficiently deaggregating calculi deposits within human body cavities and ducts. The methods and compositions of the present invention are particularly well suited for dissolving and/or deaggregating gallstones having high pigment content, including what is commonly referred to as black pigment gallstones and brown pigment gallstones. Additionally, the present invention is suitable for dissolving noncholesterol components of mixed gallstones subsequent to or prior to dissolving cholesterol portions of the mixed gallstones with effective cholesterol solvents.

The methods and compositions of the present invention are discussed in terms of their usefulness for dissolving biliary calculi having varying pigment content and other noncholesterol component content. However, those skilled in the art will appreciate that the methods and compositions disclosed herein are equally applicable to dissolving other types of pigment calculi deposits as well as combinations of calcium carbonate, calcium palmitate, calcium bilirubinate, calcium phosphate, calcium oxalate, polybilirubinates, and glycoproteins.

More particularly, the present invention provides methods for dissolving noncholesterol components of biliary calculi which include providing a solution of an effective amount of at least one quaternary ammonium salt and causing the solution to contact the biliary calculi for a length of time sufficient to dissolve a clinically acceptable amount of the noncholesterol components of biliary calculi. Preferably, the solution of quaternary ammonium salt is aqueous and has a pH of from about 6 to about 11. Moreover, the preferred embodiments of the present invention are aqueous compositions of quaternary ammonium salts and additives which further enhance the dissolution of the pigment calculi.

Suitable additives for enhancing the dissolution of biliary calculi include chelating agents and disulfide bond cleaving agents. The chelating agents contribute to deaggregating inorganic salts while the disulfide bond cleaving agents react with the disulfide bonds in the glycoproteins to produce smaller, more easily dissolved compounds. Additional additives include pH buffer agents which contribute to preparing and maintaining the solution pH within preferred ranges.

When the methods taught herein are utilized for the contact dissolution of noncholesterol components of gallstones, causing the solution of quaternary ammonium salt and additives to contact the gallstones is typically carried out using a percutaneous stick into a patient's gallbladder followed by repeatedly infusing and withdrawing the solution directly into and from the gallbladder through a lumen of a catheter. This is continued for a length of time sufficient to dissolve the pigment calculi or for a length of time sufficient to dissolve a clinically acceptable amount of the pigment calculi and other noncholesterol components of the calculi.

The compositions of the present invention can be made using standard techniques known in the art for preparing solutions. Typically, the methods include adding one or more quaternary ammonium salts and the selected additives to a liquid and stirring until complete dissolution occurs. When pH buffer agents are utilized, the pH buffer agent is generally added to the solution prior to adding the quaternary ammonium salt and additives. When necessary, the pH can be altered with an appropriate acid or base.

Further objects, features and advantages of the dissolution compositions of the present invention, as well as a better understanding thereof, will be afforded to those skilled in the art from a consideration of the following detailed explanation of preferred exemplary embodiments thereof.

BRIEF DESCRIPTION OF THE DRAWING

The figure illustrates the dissolution profile of noncholesterol components of gallstone in an exemplary composition of the present invention.

DETAILED DESCRIPTION OF PREFERRED EMBODIMENTS

In its broadest aspect, the present invention includes methods and compositions for dissolving pigment calculi utilizing liquid solutions of at least one quaternary ammonium salt. The methods and compositions of the present invention are particularly applicable for the effective treatment of biliary stone diseases, including gallstone disease, in which the stones or calculi are more than 4 wt %. Additionally, the methods and compositions of the present invention can be utilized to dissolve other noncholesterol components of biliary calculi including mineral salts and mineralized complexes. As previously described, the term pigment refers to that portion of animal calculi formed in vivo which includes aggregates of bilirubinate salts and polybilirubinates. Other noncholesterol components of biliary calculi include glycoprotein, calcium carbonate, calcium phosphate, calcium oxalate and fatty acid salts such as calcium palmitate and polybilirubinates. However, it is also within the scope of the teachings of the present invention to utilize the compositions disclosed herein to dissolve all forms of calculi deposited within body cavities and on prosthetic devices. These forms include kidney or urinary bladder stones, arterial plaque, and calcified portions of implanted devices prepared from biomaterials including heart valves, pacemaker leads, stents, breast implants, penile implants and other forms of plastic surgery prosthetics.

The present invention is based upon the discovery that liquid solutions of at least one quaternary ammonium salt will dissolve and/or deaggregate pigment calculi and other noncholesterol components of pigment calculi when the solutions are caused to come into contact with the calculi. These solutions will also dissolve pigment and other noncholesterol components of calculi having significant amounts of cholesterol. The amount of dissolution which occurs is sufficient to dissolve clinically significant amounts of the noncholesterol components of calculi. More specifically, the compositions provided by the present invention will dissolve and/or deaggregate enough of the noncholesterol components of calculi to alleviate the symptoms of the disease. Alternatively, as further described below, the practice of the present invention will result in the dissolution of enough of the pigment calculi to allow the residue to be aspirated from their enclosure.

More particularly, compositions useful for the contact dissolution of noncholesterol components of gallstones include aqueous solutions of a dissolution effective concentration of at least one quaternary ammonium salt with the solutions having a pH of from about 6 to about 11. Preferably, the solutions also include a mineral chelating agent and a disulfide bond cleaving agent. When necessary, to prepare and maintain the aqueous solution at the desired pH, the solution also includes a pH buffer agent and suitable amounts of a pH adjusting acid or base.

Quaternary ammonium salts are typically prepared by reacting ammonia or a primary, secondary, or tertiary amine with an alkyl halide to form an ionic salt of the halide ion and amine. Necessarily, there are appreciably large numbers of possible quaternary ammonium salts, and, broadly speaking, any of these salts is suitable for use in the compositions of the present invention. Particularly suitable quaternary ammonium salts include benzalkonium chloride, dodecyltrimethyl ammonium chloride, mixed trialkyl ammonium chloride, dodecyltrimethyl ammonium bromide, cetyl pyridinium chloride, trimethyl alkyl ammonium bromide, Arquad ® HTLB, Arquad ® C-33, Ceraphyl ® 65, Arquad ® 218-100P and quaternary ammonium polymers. The chemical structures of these compounds are illustrated in Table I. Of these, the preferred quaternary ammonium salts are benzalkonium chloride and dodecyltrimethyl ammonium bromide.

TABLE I

QUATERNARY AMMONIUM COMPOUND STRUCTURES

| Compound | Structure |
| --- | --- |
| benzalkonium chloride | phenyl-$CH_2-N_{\oplus}(CH_3)_2-R$ $Cl^{\ominus}$, $R = C_8H_{17}$ to $C_{18}H_{37}$ |
| cetyl pyridinium chloride | pyridinium-$N_{\oplus}-(CH_2)_{15}CH_3$ $Cl^{\ominus}$ |
| dodecyltrimethyl ammonium bromide | $CH_3-N_{\oplus}(CH_3)_2-(CH_2)_{11}CH_3$ $Br^{\ominus}$ |
| Arquad HTLB ® | $CH_3-N_{\oplus}(CH_3)(R)-R$ $^{\ominus}OSO_2OCH_3$, $R =$ ETHYLHEXYL (HYDROGENATED TALLOW) |
| Arquad C-33 ® | $CH_3-N_{\oplus}(CH_3)_2-R$ $Cl^{\ominus}$, $R =$ COCOAALKYL |
| Ceraphyl 65 ® | $R-C(=O)-NH(CH_2)_3-N_{\oplus}(CH_3)_2-CH_3CH_2OH$ $Cl^{\ominus}$, $R =$ MINK FATTY ACIDS |
| Arquad 218-100P ® | $CH_3-N_{\oplus}(CH_3)(R)-R$ $Cl^{\ominus}$, $R = C_{18}H_{37}$ |

The dissolution effective amount of quaternary ammonium salt varies with the strength of the salt and the particular combination of pigment and additional noncholesterol components in the calculi. Concentrations ranging from about 1 wt % up to about 25 wt % quaternary ammonium salt can be utilized in aqueous solutions. However, for most applications effective amounts of quaternary ammonium salts are between about 5 wt % and 10 wt %. The trialkyl monomethyl quaternary ammonium salts tend to have more limited water solubilities. Accordingly, in aqueous solutions, their concentrations may be limited by their solubility in water. Additionally, as described more fully below, in clinical applications lower concentrations are preferred in order to minimize the quantity of quaternary ammonium salt exposed to tissue.

Chelating agents, useful additives in the compositions of the present invention, enhance the dissolution of mineral components such as calcium and magnesium salts and complexes. Suitable chelating agents include ethylenediaminetetracetic acid (EDTA), ethylenediamine, triethanolamine, polyethyleneimine, dimercaptopropanol, sodium tripolyphosphate (STPP), triethylenetetramine, triethylenetetramine.2HCl. The chemical structures of these compounds are illustrated in Table II.

TABLE II

Chelating Agents

| | Structure |
|---|---|
| EDTA | NaOOCCH$_2$\NCH$_2$CH$_2$N/CH$_2$COONa, NaOOCCH$_2$/ \CH$_2$COOH |
| ethylenediamine | H$_2$HCH$_2$CH$_2$NH$_2$ |
| triethanolamine | N(CH$_2$CH$_2$OH)$_3$ |
| STPP | NaO—P(=O)(O Na)—O—P(=O)(O Na)—O—P(=O)(O Na)—ONa |
| dimercaptopropanol | CH$_2$SHCHSHCH$_2$OH |
| triethylenetetramine | (NH$_2$CH$_2$CH$_2$NHCH$_2$—)$_2$ |
| polyethyleneimine | H(NHCH$_2$CH$_2$)$_n$NH$_2$ |

Of these, preferred chelating agents are EDTA and sodium tripolyphosphate. Typically, chelating agents utilized in the compositions of the present invention are present at a concentration of from about 0.5 wt % to about 20 wt %. Preferable concentrations range from about 1 wt % to about 5 wt %.

Disulfide bond cleaving agents useful in the compositions of the present invention include n-acetyl cysteine, dithiothreitol, penicillamine and mercapto-1-methylimidazole. The chemical structures of these compounds are illustrated in Table III.

TABLE III

Disulfide Bond Cleaving Agent

| | |
|---|---|
| n-acetyl cysteine | HSCH$_2$CHCOOH \| NHCOCH$_3$ |
| penicillamine | SH NH$_2$ \| \| (CH$_3$)$_2$C—CHCOOH |
| dithiothreitol | HSCH$_2$CH—CH—CH$_2$SH \| \| OH OH |
| mercapto-1-methyl imidazole | (ring with N, N-CH$_3$, SH) |

Experimental results indicate that n-acetyl cysteine and dithiothreitol in particular enhance the dissolution of the noncholesterol components of calculi when utilized in conjunction with quaternary ammonium salt the compositions of the present invention. This enhanced dissolution is attributed to the ability of these compounds to react with disulfide bonds with glycoprotein matrices.

As mentioned above, aqueous solutions of a quaternary ammonium salt, which optionally include a chelating agent and/or a disulfide bond cleaving agent, are most effective for dissolving and/or deaggregating pigment and other noncholesterol portions of calculi when the solution has a basic pH. Accordingly, the compositions of the present invention preferably have a pH ranging from about 5 to about 11. Preferably, the solution pH is between 8 and 9.

In order to obtain and maintain a particular selected pH, the present compositions preferably include a pH buffering agent selected from any of a large number of inorganic and organic buffers. High purity pH buffers are available from many commercial sources and are well documented in the literature. Phosphate buffers are particularly suitable for use in solutions exposed to tissue, and are the preferred pH buffering agents. As will be described below, even though the compositions of the present invention include pH buffers, typically the solution pH requires additional adjustment. For this reason, these compositions can also have added pH adjusting acids or bases.

In addition to including chelating agents and disulfide bond cleaving agents, the pigment calculi and pigment gallstone dissolution properties of the present invention can be enhanced with the presence of certain amino acids, proteins, and bile acids. When present as concentrations of at least 1 wt %, these can act as surfactants, bilirubin binding agents or buffering agents. Cholic acid and chenodeoxycholic acid are particularly suitable bile acids. Arginine and carnosine are the preferred amino acids, and albumin is a preferred protein. The structures of these amino acids and bile acids are shown in Table IV.

TABLE IV

| | Structure |
|---|---|
| cholic Acid | (steroid structure with H$_3$C, HO, CH$_3$, COOH, OH groups) |
| chenodeoxycholic Acid | (steroid structure with H$_3$C, CH$_3$, COOH, HO, OH groups) |
| arginine | HN=CNHCH$_2$CH$_2$CH$_2$—C—COOH, with NH$_2$ and H substituents |
| carnosine | H$_2$NCH$_2$CH$_2$CONHCHCH$_2$—(imidazole ring), COOH |

More particularly, in accordance with the teachings of the present invention, preferred compositions useful for dissolving and/or deaggregating noncholesterol portions of biliary calculi, include phosphate buffered aqueous solutions of from 1 wt % to 25 wt % of at least one quaternary ammonium salt selected from the group consisting of benzalkonium chloride and dodecyltrimethyl ammonium bromide, from 0.5 wt % to 15 wt % EDTA and from 1 wt % to 10 wt % of at least one disulfide bond cleaving agent selected from the group consisting of n-acetyl cysteine and penicillamine. These preferred compositions have a pH of from about 8 to about 9. A preferred embodiment of the present invention is an aqueous solution of about 5 wt % dodecyltrimethyl ammonium bromide, about 3 wt % EDTA and about 2 wt % n-acetyl cysteine, phosphate buffered to a pH of 9.

The compositions of the present invention can be utilized in accordance with any of a number of techniques for the dissolution and/or deaggregation of biliary calculi, particularly gallstones. These techniques include providing a solution which includes at least one quaternary ammonium salt and then causing the solution to contact the biliary calculi for a length of time sufficient to dissolve a clinically acceptable amount of the pigment and additional noncholesterol components of the biliary calculi. Preferably, and as described above, the solutions are phosphate buffered aqueous solutions and further include at least one chelating agent and at least one disulfide bond cleaving agent.

Causing the solution to contact the calculi can be carried out using methods for perfusing liquids into enclosed cavities such as hollow ducts, organs or even arterial systems of a patient. Such methods include but are not limited to percutaneous catheter placement, endoscopic retrograde biliary catheter placement, or placement of a catheter in a localized area by surgical means. Following catheter placement, the solution is flushed through the catheter and into the cavity where it contacts the pigment calculi. The solution and dissolved portions of pigment are then removed through the catheter and fresh solution is perfused into the cavity. This perfusing technique is typically accomplished using a syringe or pumping system.

The methods and compositions of the present invention are particularly useful for the dissolution of noncholesterol calculi deposits in the gallbladder and less frequently in the biliary tract. However, it is contemplated to be within the scope of the present invention to utilize the disclosed compositions for the in vitro dissolution or deaggregation of calculi, particularly pigment and additional noncholesterol components of calculi. Accordingly, these compositions are also useful for dissolving combinations of calcium carbonate, calcium phosphate, calcium oxalate, calcium palmitate, calcium bilirubinate, polybilirubinates, glycoproteins, artificial biliary stones and retrieved biliary stones.

In practicing the methods of the present invention, lengths of time which are sufficient to dissolve and/or deaggregate a clinically acceptable amount of the noncholesterol portions of calculi vary and can depend upon the type of pigment, the amount and type of other noncholesterol components, as well as the number and size of the calculi deposits. Furthermore, in vivo applications require time considerations which are different from the times required for in vitro applications. Clinically, the contact dissolution of stones using perfusion techniques can require more than one treatment procedure with each treatment procedure requiring up to 8 hours. Treatment procedures can extend over a period of several days.

The compositions and methods of the present invention can also be utilized in conjunction with techniques for dissolving cholesterol portions of mixed calculi. This approach is particularly suitable when dissolving calculi having layers of cholesterol alternating with layers of noncholesterol components, including layers of pigment and mineral salts. For example, to effectively dissolve multilayered gallstones with an outer cholesterol layer, methyl-t-butyl ether can be brought into contact with the calculi for a length of time sufficient to dissolve a clinically sufficient amount of the cholesterol layer. Subsequently, causing a solution of at least one quaternary ammonium salt to contact the calculi will dissolve and/or deaggregate the layer of noncholesterol components. These steps are repeated until the calculi is sufficiently dissolved.

The just described techniques for dissolving layered calculi can also be utilized to dissolve the noncholesterol portions of cholesterol rich calculi. That is, the cholesterol portion of cholesterol rich calculi can be removed from the calculi by contacting the calculi with at least one cholesterol solvent such as MTBE. Then the noncholesterol components, including pigment and mineralized portions, can be removed by contacting the remaining calculi with compositions taught by the present invention.

The compositions of the present invention can be prepared using techniques for dissolving solids in liquids. Typically these techniques include adding a selected amount of at least one solute, for example, quaternary ammonium salt, chelating agent, and disulfide cleaving agent, to a liquid followed by stirring. Generally, it is not necessary to heat the composition to form a solution. Additionally, some quaternary ammonium salts are commercially available in aqueous solutions. When preparing solutions which include these sources of quaternary ammonium salts, the appropriate amount of commercial solution is selected and the amount of water is correspondingly taken into account.

It is generally preferred to use pH buffered aqueous solutions to prepare the compositions of the present invention rather than to add the buffer after the solutes are added. Thus, for example, to make solutions having a pH of 8, a stock solution of phosphate buffer having a pH of 8 and a buffering capacity suitable for maintaining the pH of the solution at 8 is first prepared and the remaining solutes are then added. As mentioned above, the pH buffered solutions typically required an additional pH adjustment. This can be accomplished by adding enough strong base or acid to raise or lower the pH. In most cases small amounts of a strong base are added to raise the pH.

The following non-limiting examples further illustrate methods for preparing the compositions of the present and invention and their in vitro utility.

EXAMPLE 1

Dissolution of Gallstone Pigment Powder with Aqueous Quaternary Ammonium Salt

A 5 wt % solution of dodecyltrimethyl ammonium bromide was prepared in aqueous phosphate buffer by adding 0.5 grams of the salt to 10 mL of 0.1M phosphate buffer adjusted to pH 8. Gallstone pigment powder residue was prepared by extracting gallstones retrieved from a number human gallbladders following cholecystectomy with methyl-t-butyl ether to remove the cholesterol portion of the stones and leaving only the pigment portions and other noncholesterol of the gallstones.

Approximately 5 mg of the gallstone powder was gravimetrically transferred to the 10 mL of 5 wt % dodecyltrimethyl ammonium bromide and the mixture was shaken in a water bath at 30° C. After 4 hours the mixture was filtered through a 5–8 micron filter, the filter dried, and the residue weighed to determine the amount of dissolution. Results showed that 20.8±10% of the gallstone powder dissolved in the quaternary ammonium salt solution.

EXAMPLE 2

Dissolution of Gallstone Powder and Calculi Components with EDTA and Quaternary Ammonium Salts Aqueous solutions of quaternary ammonium salts were prepared by adding 1 g of salt to 10 mL of 1 wt % EDTA in 0.1M phosphate buffer adjusted to pH 8. In order to qualitatively determine the degree to which calcium bilirubinate, gallstone powder, and bilirubin solutes dissolve in each solution, 1–2 mg of each of these solutes was transferred to each of about 1 mL of the aqueous solutions. The degree of dissolution was assessed after initial mixing. The source of the noncholesterol portion of gallstone was the same as that described in Example 1. Table V illustrates the qualitative degree of dissolution of each of the solutes in the tested solutions.

TABLE V

| Agent | Ca Bilirubinate | Noncholesterol Residue | Bilirubin |
| --- | --- | --- | --- |
| 10% benzalkonium bromide | dissolved | very high amount dissolved | dissolved |
| 10% dodecyltrimethyl ammonium bromide | dissolved | very high amount dissolved | dissolved |
| 10% methyl mixed trialkyl ammonium chloride in MtBE | dissolved | very high amount dissolved | dissolved |

EXAMPLE 3

Dissolution of Gallstone Pigment Powder in Aqueous Solutions of Quaternary Ammonium Salt, EDTA, and Disulfide Bond Cleaving Agent Solutions of a quaternary ammonium salt, EDTA, and a disulfide bond cleaving agent were prepared in an aqueous 0.1M phosphate buffer. With the exception of one solution, all the solutions were adjusted to a pH of 8. The general technique described in Example 1 was utilized to prepare the solutions. Samples of between 5 and 15 mg of the noncholesterol portion of gallstones described in Example 1 were transferred to 10 mL of each solution and the mixtures were mixed in a water shaker for 4 hours at 30° C. The mixtures were filtered with a 5–8 micron filter and the undissolved residue and filter were then dried and weighed to gravimetrically determine the amount of powder dissolved. The ultraviolet absorption at 450 nm of the filtrate was also measured. The absorption at this wavelength is primarily due to the presence of bilirubin compounds and gives an indication of the relative strength of the solution for absorbing those compounds.

Table VI details the results of these dissolution experiments and further illustrates their usefulness for dissolving the pigment portion of gallstones. Normalized UV absorbance refers to the UV absorbance of the filtrate after adjustment for the initial weight of starting material.

TABLE VI

| Solution | Normalized UV Absorbance | % Dissolution |
| --- | --- | --- |
| 5% benzalkonium chloride<br>1% EDTA<br>pH 8 | 0.82 ± 0.11 | 13 ± 5 |
| 5% benzalkonium chloride<br>1% EDTA<br>1% dithiothreitol<br>2% arginine<br>pH 8 | 0.87 ± 0.11 | 19 ± 2.5 |
| 5% benzalkonium chloride<br>1% EDTA<br>2% dithiothreitol<br>pH 8 | 0.83 ± 0.13 | 22 ± 12 |
| 5% dodecyltrimethyl ammonium bromide<br>1% EDTA<br>2% penicillamine<br>pH 8 | 1.5 ± 0.13 | 53 ± 7 |
| 3% EDTA<br>5% dodecyltrimethyl ammonium bromide<br>2% n acetyl cysteine<br>pH 9.0 | 1.23 ± 0.22 | 59.3 ± 0.6 |
| 1% STPP<br>5% dodecyltrimethyl ammonium bromide<br>2% n acetyl cysteine<br>pH 8 | 1.52 ± 0.24 | 42 ± 11 |
| 5% CPC<br>2% n acetyl cysteine<br>1% EDTA<br>pH 8 | 1.1 ± 0.06 | 45.5 ± 8.3 |
| 5% Arquad C-33 ®<br>2% n acetyl cysteine<br>1% EDTA<br>pH 8 | 0.79 ± 0.02 | 35 ± 8.0 |
| 5% Arquad HTLB ®<br>2% n acetyl cysteine<br>1% EDTA<br>pH 8 | 0.84 ± 0.0 | 34.2 ± 8.2 |
| 5% Ceraphyl 65 ®<br>2% n acetyl cysteine<br>1% EDTA<br>pH 8 | 0.71 ± 0.00 | 28.2 ± 5.6 |

EXAMPLE 4

Comparison of Gallstone Pigment Dissolution in Known Solutions with that of the Compositions of the Present Invention Renacidin ®, a commercially available acidic solution for dissolving kidney stones was evaluated for its ability to dissolve the noncholesterol portion of human gallstones. The same technique for quantitatively determining the amount of dissolution used in Example 3 was utilized in this experiment. The source of the pigment portion of human gallstones was the same as the previous 3 examples.

Renacidin ® dissolved 42.4±4.1% of the pigment portion of human gallstones. The normalized UV absorbance of the filtrate was <0.010 indicating that essentially nonbilirubin components were dissolved.

EXAMPLE 5

Dissolution of Pigment Calculi over Time

A solution of 5 wt % dodecyltrimethyl ammonium bromide, 1 wt % EDTA and 2 wt % n-acetyl cysteine was prepared in 0.1M phosphate buffer adjusted to pH 8. Ten mL of the solution was added to 10-15 mg of noncholesterol gallstone. The amount of gallstone powder which dissolved with time was determined over a 48 hour period. FIG. 1 illustrates that the majority of the amount of gallstone powder which dissolved went into solution during the first 4 hours. However, the dissolution continued to occur over the full 48 hours.

The compositions of the present invention exhibit an enhanced ability to dissolve calculi and especially the pigment and other noncholesterol portions of cholesterol rich gallstones and pigment rich gallstones. This enhanced ability is attributed to the quaternary ammonium salts. While the mechanism of this enhanced ability is not clear, it could be the result of the non-polar portion of the quaternary ammonium salts, the alkyl or benzyl functionalities, interacting with the non polar pyrrole groups of the bilirubin. Additionally, the charged nitrogen could be interacting with the carboxylic acid functionalities on the bilirubin compounds of the pigment.

Having thus described exemplary embodiments of the present invention, it should be noted by those skilled in the art that the disclosures herein are exemplary only and that alternatives, adaptations and modifications may be made within the scope of the present invention.

We claim:

1. A process for the dissolution of noncholesterol pigment components of biliary calculi, said calculi located within a body biliary tract, and said process comprising the steps of:
   providing a composition comprising an aqueous solution of at least one quaternary ammonium salt selected from the group consisting of benzalkonium chloride, dodecyltrimethyl ammonium chloride, dodecyltrimethyl ammonium bromide, cetylpyridinium chloride, trimethylalkylammonium bromide, methyl mixed trialkyl ammonium chloride and quaternary ammonium polymers, said quaternary ammonium salt being present in said composition at a dissolution effective concentration; and
   perfusing said composition into said biliary tract to cause said composition to contact said biliary caculi for a length of time sufficient to dissolve a clinically acceptable amount of said noncholesterol pigment portions of said calculi.

2. The process of claim 1 wherein said composition has a pH of between about 6 and about 11.

3. The process of claim 1 wherein said dissolution effective concentration is from about 1 wt % to about 25 wt %.

4. The process of claim 1 wherein said composition further includes a chelating agent.

5. The process of claim 4 wherein said chelating agent is selected from the group consisting of EDTA, sodium tripolyphosphate, ethylenediamine, triethanolamine, polyethyleneimine, dimercaptopropanol, and triethylenetetramine.

6. The process of claim 1 wherein said composition further includes a disulfide bond cleaving agent.

7. The process of claim 6 wherein said disulfide bond cleaving agent is selected from the group consisting of dithiothreitol, mercapto-1-methyl imidazole, penicillamine, and N-acetyl cysteine.

8. The process of claim 1 wherein said noncholesterol components of calculi comprises combinations of calcium bilirubinate, calcium carbonate, bilirubin polymers, calcium palmitate, glycoproteins, calcium phosphate and calcium oxalate.

9. A process for the dissolution of noncholesterol pigment components of biliary calculi, said process comprising the steps of:
   providing a composition comprising an aqueous solution of at least 1 wt % of at least one quaternary ammonium salt selected from the group consisting of benzalkonium chloride, dodecyltrimethyl ammonium chloride, dodecyltrimethyl ammonium bromide, cetylpyridinium chloride, trimethylalkylammonium bromide, methyl mixed trialkyl ammonium chloride and quaternary ammonium polymers, said aqueous solution having a pH of from about 6 to about 11; and
   causing said composition to contact said biliary calculi for a length of time sufficient to dissolve a clinically acceptable amount of said noncholesterol components of said calculi.

10. The process of claim 9 wherein said aqueous solution further includes a pH buffer, said pH buffer selected from the group consisting of inorganic and organic pH buffering compounds.

11. The process of claim 9 wherein said composition further includes 0.1 to about 15 wt % of chelating agent.

12. The process of claim 11 wherein said chelating agent is selected from the group consisting of EDTA, sodium tripolyphosphate, ethylenediamine, triethanolamine, polyethyleneimine, dimercaptopropanol, and triethylenetetramine.

13. The process of claim 9 wherein said composition further includes from about 1 wt % to about 10 wt % of disulfide bond cleaving agent.

14. The process of claim 13 wherein said disulfide bond cleaving agent is selected from the group consisting of dithiothreitol, mercapto-1-methyl imidazole, penicillamine, and n-acetyl cysteine.

15. The process of claim 9 wherein causing said composition to contact said pigmented gallstone is accomplished by inserting a catheter into a gallbladder and infusing said composition through said catheter into said gallbladder.

* * * * *